US008175683B2

(12) United States Patent
Roose (10) Patent No.: US 8,175,683 B2
(45) Date of Patent: May 8, 2012

(54) SYSTEM AND METHOD OF DESIGNING AND MANUFACTURING CUSTOMIZED INSTRUMENTATION FOR ACCURATE IMPLANTATION OF PROSTHESIS BY UTILIZING COMPUTED TOMOGRAPHY DATA

(75) Inventor: Jeffrey Robert Roose, Milford, IN (US)

(73) Assignee: DePuy Products, Inc., Warsaw, IN (US)

( * ) Notice: Subject to any disclaimer, the term of this patent is extended or adjusted under 35 U.S.C. 154(b) by 2901 days.

(21) Appl. No.: 10/748,316

(22) Filed: Dec. 30, 2003

(65) Prior Publication Data

US 2005/0148843 A1 Jul. 7, 2005

(51) Int. Cl.
*A61B 5/00* (2006.01)

(52) U.S. Cl. ........ 600/427; 623/911; 623/923; 700/120; 382/128; 600/587; 128/920

(58) Field of Classification Search .......... 700/120; 606/102; 623/911, 923, 919, 20.14; 600/427, 600/587
See application file for complete search history.

(56) References Cited

U.S. PATENT DOCUMENTS

| | | | |
|---|---|---|---|
| 4,275,444 A | 6/1981 | Ryan | |
| 4,436,684 A | 3/1984 | White | |
| 4,506,393 A | 3/1985 | Murphy | |
| 4,704,686 A | 11/1987 | Aldinger | |
| 4,936,862 A | 6/1990 | Walker et al. | |
| 5,007,936 A | 4/1991 | Woolson | |
| 5,360,446 A | 11/1994 | Kennedy | |
| 5,370,692 A * | 12/1994 | Fink et al. ..................... | 128/898 |
| 5,408,409 A | 4/1995 | Glassman et al. | |
| 5,735,277 A | 4/1998 | Schuster | |
| 5,741,215 A | 4/1998 | D'Urso | |
| 5,768,134 A | 6/1998 | Swaelens et al. | |
| 5,798,924 A | 8/1998 | Eufinger et al. | |
| 5,824,083 A | 10/1998 | Draenert | |
| 5,824,085 A | 10/1998 | Sahay et al. | |
| 5,857,853 A | 1/1999 | Van Nifterick et al. | |
| 5,995,738 A | 11/1999 | DiGioia, III et al. | |
| 6,002,859 A | 12/1999 | DiGioia, III et al. | |
| 6,112,109 A | 8/2000 | D'Urso | |
| 6,177,034 B1 | 1/2001 | Ferrone | |
| 6,205,411 B1 | 3/2001 | DiGioia, III et al. | |
| 6,254,639 B1 | 7/2001 | Peckitt | |
| 6,327,491 B1 | 12/2001 | Franklin et al. | |
| 6,458,161 B1 | 10/2002 | Gibbs et al. | |
| 6,464,639 B1 | 10/2002 | Kim et al. | |
| 6,849,223 B2 * | 2/2005 | Dean et al. ..................... | 264/400 |
| 6,923,817 B2 * | 8/2005 | Carson et al. ................. | 606/130 |
| 2002/0123817 A1 | 9/2002 | Clasbrummel et al. | |
| 2002/0147455 A1* | 10/2002 | Carson .......................... | 606/130 |
| 2003/0114936 A1* | 6/2003 | Sherwood et al. .......... | 623/23.58 |

(Continued)

*Primary Examiner* — Brian Casler
*Assistant Examiner* — Amanda Lauritzen
(74) *Attorney, Agent, or Firm* — Maginot, Moore & Beck (57) ABSTRACT

A method and system may be used to design and control the manufacture of a surgical guide for implanting a prosthetic component. The system includes a bone surface image generator, a surgical guide image generator, and a surgical guide image converter. The bone surface image generator receives three dimensional bone anatomical data for a patient's bone and generates a bone surface image. The surgical guide image generator generates a surgical guide image from the bone surface image and an image of a prosthesis imposed on the bone surface image. The supporting structure of the generated surgical guide image conforms to the surface features of the three dimensional bone surface image. The surgical guide image is converted by surgical guide image converter into control data for operating a machine to form a surgical guide that corresponds to the surgical guide image.

20 Claims, 7 Drawing Sheets

U.S. PATENT DOCUMENTS

| | | |
|---|---|---|
| 2003/0212459 A1 | 11/2003 | Gibbs |
| 2003/0216669 A1* | 11/2003 | Lang et al. .................... 600/587 |
| 2003/0236473 A1* | 12/2003 | Dore et al. .................... 600/587 |
| 2004/0138754 A1* | 7/2004 | Lang et al. ................. 623/20.14 |
| 2004/0243481 A1* | 12/2004 | Bradbury et al. ................ 705/26 |
| 2007/0167741 A1* | 7/2007 | Sherman et al. ............... 600/424 |
| 2007/0173815 A1* | 7/2007 | Murase ........................... 606/53 |
| 2007/0198022 A1* | 8/2007 | Lang et al. ...................... 606/88 |

* cited by examiner

SYSTEM AND METHOD OF DESIGNING AND MANUFACTURING CUSTOMIZED INSTRUMENTATION FOR ACCURATE IMPLANTATION OF PROSTHESIS BY UTILIZING COMPUTED TOMOGRAPHY DATA

FIELD OF THE INVENTION

The present invention relates to prosthetic systems for the replacement of joints or portions thereof. More particularly, the invention concerns customized instrumentation, and a method of designing and manufacturing such instrumentation based upon computed tomography data obtained from the patient.

BACKGROUND OF THE INVENTION

For treatment of various problems with the shoulder and hip such as degenerative arthritis and trauma, one method of providing relief to a patient is to replace the articulating surfaces of a diseased joint with an artificial or prosthetic joint. In the case of a shoulder, the humerus and glenoid articulating surfaces may be replaced. In the case of a hip, the femur and acetabulum articulating surfaces may be replaced.

In such replacement, pain relief, increased motion and anatomic reconstruction of the shoulder or hip joint are goals of the orthopaedic surgeon. With multiple variations in human anatomy, prosthetic systems need to accurately replicate the joints that they replace and maintain the natural symmetry of the joints on the left and right sides of the patient's body.

A hip replacement procedure may involve a total hip replacement or a partial hip replacement. In a total hip replacement procedure, a femoral component having a head portion is utilized to replace the natural head portion of the thighbone or femur. The femoral component typically has an elongated intramedullary stem which is utilized to secure the femoral component to the patient's femur. In such a total hip replacement procedure, the natural bearing surface of the acetabulum is resurfaced or otherwise replaced with a cup-shaped acetabular component that provides a bearing surface for the head portion of the femoral component.

Acetabular cups may be secured to the acetabulum in a number of different ways. For example, an acetabular cup may be secured to the acetabulum by the use of bone cement. However, recent studies have speculated that it may be desirable to secure artificial components to natural bone structures without the use of bone cement. Hence, a number of press fit acetabular cups have been designed for implantation without the use of cement.

Regardless as to whether cement is used or not, a surgeon typically uses a surgical tool called a reamer to ream the acetabulum and create a cavity into which the acetabular cup is secured. One problem that surgeons encounter is being able to properly match the size of the reamer to the desired acetabular cup size.

Although press fitted acetabular cups are typically described as being "generally hemispherical" in shape, such cups, in reality, are sub-hemispherical. A sub-hemispherical configuration suffers from a number of limitations. For example, a surgeon may have difficulty in reaming a properly sized cavity for an acetabular cup that is not truly hemispherical. This difficulty arises because the cutting heads of reamers are typically configured as relatively true hemispheres. Hence, when a surgeon reams the patient's acetabulum, the surgeon has to "estimate" the approximate depth of the reamed recess. If the surgeon reams too much of the bone, the annular rim of the acetabular cup sits too deeply within the cavity. Conversely, if the surgeon reams too shallowly (i.e. "under reams"), the acetabular cup does not fully seat in the reamed cavity of the acetabulum. Because a surgeon may occasionally select a reamer that is slightly smaller than the acetabular cup to be implanted, under reaming may also disadvantageously lead to bone fracture of the acetabulum since excessive force may be used to insert the cup into the undersized (i.e., under reamed) cavity. Some of the early bone cups held in place by cement did not suffer from this problem because they were more accurately shaped as "true" hemispheres. However, the use of cups requiring cement for implantation is now considered undesirable.

Another drawback associated with press fitted acetabular cups relates to the configuration of the outer shell. In particular, in an attempt to increase retaining forces, a number of acetabular cups have been designed with a flared rim (known as dual radius or "bubble" cups) or a frusto-conically shaped annular rim portion (known as dual-geometry cups). Although the configuration of such cups may generate relatively strong retention forces at the rim portion of the cup, surface contact and therefore retention forces are relatively small at the portions of the outer shell other than the rim portion, particularly in the dome area. Moreover, such reduced surface contact at the portions of the outer shell other than the rim portion reduces bone ingrowth in such portions.

With the above-mentioned press fitted acetabular cups, a two-part reaming process is typically necessary. The two-part reaming process involves reaming the acetabulum with a relatively small reamer and then increasing the size of the cavity with a larger reamer. The more reaming, the more likely that a problem will occur. For example, many conventional cementless acetabular cup systems use a cup that is two millimeters larger than the last reamer size used. Inserting this size cup into the undersized reamed acetabulum to accommodate this system is sometimes difficult, particularly with resistance in the dome area of the cup, which is also larger than the last reamer size used.

Generic forms of acetabular cups are more difficult to accurately place in a joint because they are not uniquely designed and manufactured to conform to a patient's joint structure. One factor affecting accurate acetabular cup placement is the frequency with which some orthopedic surgeons encounter joint replacement surgery. Demographics in some regions may make joint replacement surgery in some regions a more common component of a surgeon's practice. However, a majority of the joint replacement surgeries are performed by surgeons for whom such surgeries are an occasional rather than stable component of their practice. That is, their relative lack of experience makes proper component placement more difficult for them as they are not as familiar with the anatomical landmarks and how they are to be aligned with the prosthetic components. Proper sighting is encumbered by the alteration of the joint's appearance by reaming and other surgical procedures required to prepare the joint for implantation of the replacement parts.

Proper orientation and implantation of generic prosthetic components may be facilitated by use of interoperative guides or templates. A guide may be a jig that is designed to temporarily attach to anatomical landmarks in the region of the joint and is configured to permit a prosthetic component to be inserted through an opening in only one orientation. Thus, the jig assists a surgeon in correlating the view of the surgical sight through the incision to the pre-operative template. A pre-operative template is an image or model of the patient's joint that is staged to take the surgeon from the state of the joint upon entry through the incision to its preparatory stages to the final scene of the implanted prosthesis.

In order for a jig to be an effective aid, however, it must first be accurately placed in the area being reconstructed. The attachment structure of the jig must be configured so it mates to unique enough bone structure to ensure its proper placement with respect to the surgical site without interfering with the working area at the site. If the jig is made with an assumption that patient anatomical structure is generally the same, then the jig may not be placed accurately enough to ensure that component orientation is optimal within the joint. Templates, while useful for pre-surgery planning and development of a surgical plan, may not be useful once the surgeon begins reconstructive work on the joint. Alteration of the surgical site by reaming and positioning of surgical instruments within the site may obscure the surgeon's view. Thus, the surgeon may have trouble envisioning how the reconstructed joint is conforming to the pre-operative plan embodied in a template.

Consequently, there is a need for a method of designing and manufacturing a surgical guide that addresses these and other drawbacks. With respect to the hip joint, there is a particular need for a surgical guide, such as a jig, and associated method of making a surgical guide that overcomes one or more of the above-mentioned problems. More particularly, what is needed is a surgical guide for placement of an acetabular prosthesis and associated method of fabrication that enables the acetabular cup to be properly oriented with respect to the reconstructed acetabulum of the innominate bone.

There is also a need for a surgical guide and associated method of fabrication that provides structure for accurately placing the jig in the vicinity of the surgical site for proper orientation of a replacement component without interfering with a surgeon's access or view of the site. Again, with respect to the hip, a need remains for a surgical guide for an acetabular prosthesis and associated method of fabrication that provides. proper angular orientation of an acetabular cup within a reconstructed acetabulum of the innominate bone without impeding access to the reconstruction area or its view.

SUMMARY OF THE INVENTION

In order to address these needs, the present invention provides a method for designing and making a surgical guide for a joint socket in which bone anatomical data regarding a patient's joint is used to design and make the surgical guide. A method for designing a surgical guide for a joint replacement prosthesis comprises generating a bone surface image from three dimensional bone anatomical data corresponding to a patient's bone, generating a surgical guide image from the generated bone surface image and an image of a prosthetic imposed on the bone surface image, and generating control data from the surgical guide image so that the operation of a machine for fabricating a surgical guide may be controlled to produce a surgical guide that corresponds to the surgical guide image. The three dimensional bone anatomical data may be computed tomography data of a bone in which a prosthesis corresponding to the prosthetic image will be implanted. The surgical guide image generation may also include integrating at least one marker slot in the surgical guide image. The method of the present invention may also include controlling a laser with the generated control data to selectively crystallize a resin to form a surgical guide that corresponds to the surgical guide image. The method may also be used to control operation of a machine tool to selectively cut a solid material to form a surgical guide that corresponds to the surgical guide image. The solid material may be polyethylene or the like. When the control data is used to control a laser, the control data is preferably provided in a stereolithography file.

The method of the present invention enables the surgical guide to be fabricated with structure that conforms to the bony surface of the patient in the vicinity of the joint being reconstructed. The method enables the bony structure on which the surgical guide will rest to be selected so that the guide conforms with anatomical reference points that are not within the surgical site being reconstructed yet contribute to the surgeon's ability to properly oriented a prosthesis with respect to the site.

The present invention also includes a method for designing and making a surgical guide for positioning an acetabular cup within an acetabulum bone. The method for designing a surgical guide for positioning an acetabular cup within an acetabulum bone comprises generating an acetabulum bone surface image from three dimensional bone anatomical data of a patient's acetabulum, generating an acetabular cup jig image from the acetabulum bone surface image and an image of an acetabular cup, and generating control data from the acetabular cup jig image for controlling the operation of a machine to fabricate an actabular cup jig that corresponds to the acetabular cup jig image. The three dimensional bone anatomical data may be computed tomography data of a patient's acetabulum bone in which a prosthesis corresponding to the acetabular cup jig image will be implanted. The acetabular jig image generation may also include integrating at least one marker slot in the acetabular jig image. The method of the present invention may also include controlling a laser with the control data to selectively crystallize a resin to form the acetabular jig that conforms to a portion of the patient's acetabulum bone corresponding to the three dimensional bone data. The control data for controlling a laser to fabricate an acetabular cup jig is preferably stereolithography data. The method may also include controlling a machine tool with the control data to selectively cut a solid material to form the acetabular jig that conforms to the acetabular cup jig image. The solid material may be polyethylene or the like. The method of the present invention enables the acetabular cup jig to be formed with flanges that conform to the bony surface of the patient's acetabulum. This placement helps a surgeon to see the proper angular orientation of the acetabular cup and ream the cavity in the acetabulum for the cup accordingly.

Preferably, the acetabular cup image includes at least one marker slot and most preferably includes three marker slots. The marker slots are formed in the cup portion of the jig proximate each of three flanges used to support the acetabular jig on the acetabulum. By inscribing a reference line on the acetabulum through a marker slot and also inscribing a reference line in the acetabulum in the areas of the bone adjacent the marker slots, a surgeon is able to inscribe a staggered line on the acetabulum bone where the rim of the acetabular cup should rest. These reference marks facilitate a surgeon's ability to conform placement of the acetabular cup to the pre-operative plan template.

A system made in accordance with the principles of the present invention includes a bone surface image generator for generating a bone surface image from three dimensional bone anatomical data for a patient, a surgical guide image generator for generating a surgical guide from the bone surface image and an image of a prosthesis to be implanted in the patient's bone, and a surgical guide image converter for converting the surgical guide image into control data so that a fabricating machine may be controlled to form a surgical guide that corresponds to the surgical guide image. The bone surface image generator may use the surface slices of a CT scan series for a patient's bone to generate a bone surface image. The surgical guide image generator may be a commercially available component of a CAD system that converts three dimensional image data into CAD data and generates the supporting structure of the surgical guide image so it complements the prominent bony structure in the vicinity where a prosthetic component will be installed. The surgical guide image generator may be used to rotate the supporting structure to find an optimal orientation of the surgical guide from a CAD system operator's perspective. Once the surgical guide image is generated, the CAD file describing the image may be converted into a control data file, such as a stereolithography file. The stereolithography file may be used to control a laser of a stereolithography system to selectively crystallize a resin to form a surgical guide that corresponds to the surgical guide image. Such a system may also be used to control the operation of a machine tool to form a surgical guide from solid material, such as polyethylene.

The surgical guide image may also be used with a system for aiding a surgeon during a joint replacement surgery. The surgical assistance system includes a patient bone data repository for storage of three dimensional bone data regarding a patient's bone, a reference pointer, a registration module for correlating surface data stored in the patient bone data repository with points on a patient identified by the reference pointer, and an image generator for generating an image of the surgical site from the three dimensional data with an imposed image of a prosthetic component. The system enables a surgeon to view a perspective of the surgical site aligned with the reference pointer so that the surgeon may view how the prosthetic component should look in the site once the prosthetic component is implanted. The system may also include storage for pre-operative templates that may be imposed on an image of the surgical site generated by the image generator. The templates imposed on the image enable a surgeon to envision what remains to be done to a patient's joint to properly prepare it for implantation of the prosthetic component. Because the surgeon has used the pre-operative templates to prepare for the surgery, the assistance system of the present invention helps prevent disorientation regarding the restructuring of the surgical site that may arise as the appearance of the site changes during reconstruction.

One advantage of the present invention is that a surgical guide may be designed and manufactured in a way that quickly and accurately attaches the guide at the surgical site so a prosthetic component may be easily oriented at the joint for optimal placement.

Another advantage of the present invention is that a surgical guide may be designed and manufactured to conform to the bony structure surrounding a cavity for receiving an acetabular cup so the cup is properly oriented with respect to the reconstructed acetabulum of the innominate bone.

Another advantage of the present invention is that a surgical guide may be designed and manufactured so the supporting structure of the guide does not interfere with a surgeon's access or view of the site.

A further advantage is that the surgical guide may be quickly fabricated, thereby reducing the lead-time required from the request for surgery to the actual surgery. A still further advantage is that the templates used to prepare a surgeon for a joint replacement surgery may be used during the surgery to more fully utilize the surgeon's preparation for the surgery.

DESCRIPTION OF THE FIGURES

Corresponding reference characters indicate corresponding parts throughout the figures.

DETAILED DESCRIPTION OF THE INVENTION

For the purposes of promoting an understanding of the principles of the invention, reference will now be made to the environment and embodiments of the invention illustrated in the drawings and described in the following written specification. No limitation to the scope of the invention is thereby intended. The present invention includes any alterations and modifications to the illustrated embodiments and includes further applications of the principles of the invention as would normally occur to one skilled in the art to which this invention pertains.

In order to perform the method of the present invention, bone anatomical data is required. One way of obtaining this bone anatomical data is to perform a CT series on the patient in the area to be reconstructed. For a hip replacement, the patient is preferably scanned from the superior rim of the pelvis to the most inferior portion of the ischium in approximately 3 mm slices. Larger slices may not provide the detail in bone structure that is necessary for properly fitting a surgical guide in or near the surgical site. The CT bone anatomical data may be converted into a three dimensional image of a patient's bone. This conversion may be accomplished with a computer program, such as the Mimics program that is sold by Materialise U.S.A. of Ann Arbor, Mich. The three dimensional image may be provided to a CAD system, such as the one manufactured by Unigraphics Solutions, Inc. of Cypress, Calif. This system includes a computer program called Imageware, which receives three dimensional image data and generates a surface image of the bone such as the partial images of the pelvis shown in FIGS. 1a, 1b, and 1c.

Figure 1A:
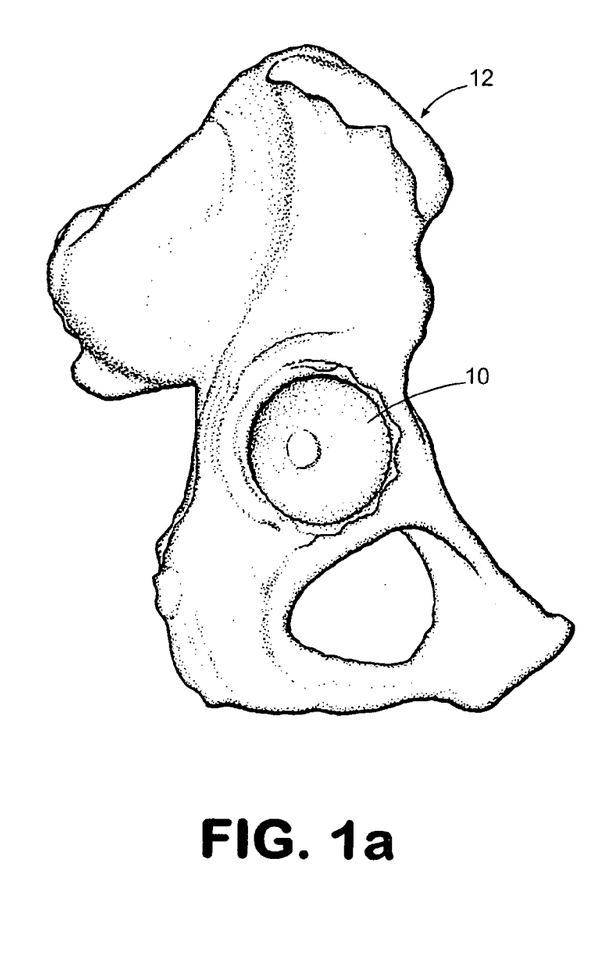
FIGS. 1a, 1b, and 1c are perspective views of a bone surface image with an acetabular implant positioned to plan.
Figure 1B:
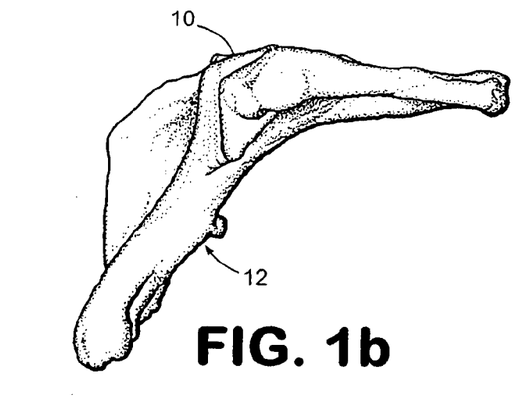
Figure 1C:
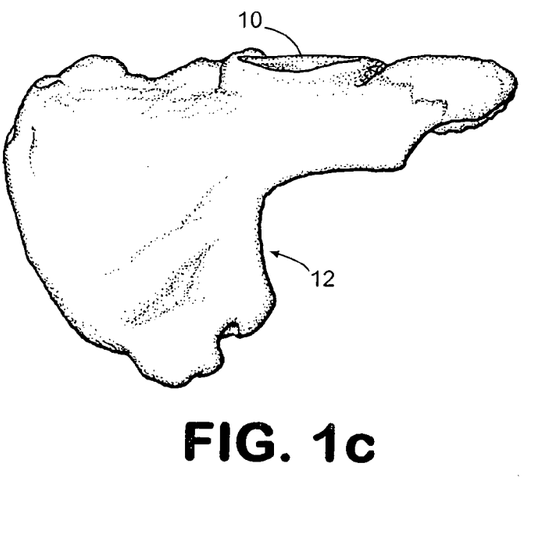

FIG. 1a presents a lateral view of a pelvis surface 12 as it is centered about the acetabulum. FIG. 1b is a distal view of the acetabulum surface while FIG. 1c is a posterior view of the same bone surface. This software may be used to integrate an acetabular cup image 10 within the acetabulum 14 as shown in FIG. 1a to form a template for pre-operative surgery planning. One advantage of the pre-operative planning made possible by the present invention is that the surgical guide enables a surgeon to properly prepare a joint bone so a prosthesis may be more easily press fitted into the bone.

Figure 2A:
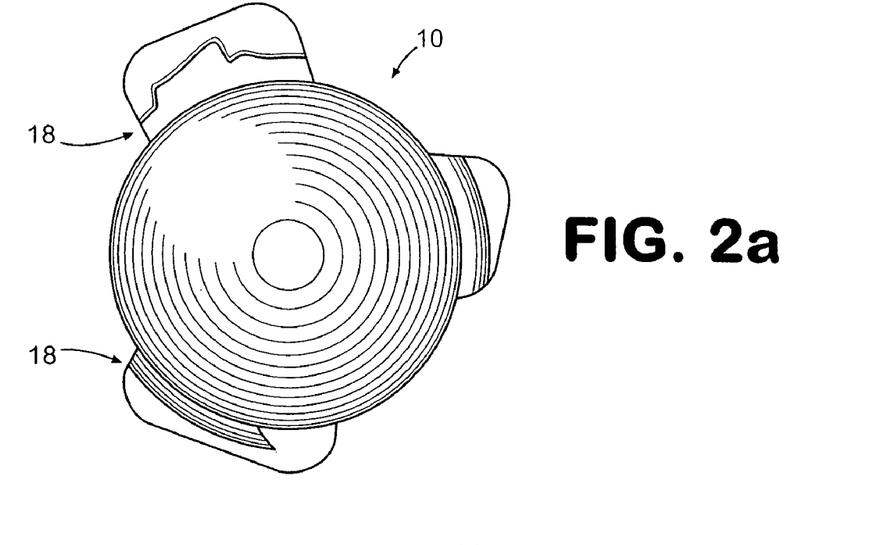
FIGS. 2a, 2b, and 2c are perspective views of a surgical guide image integrated with the acetabular implant positioned to the plan of FIGS. 1a, 1b, and 1c, respectively.
Figure 2B:
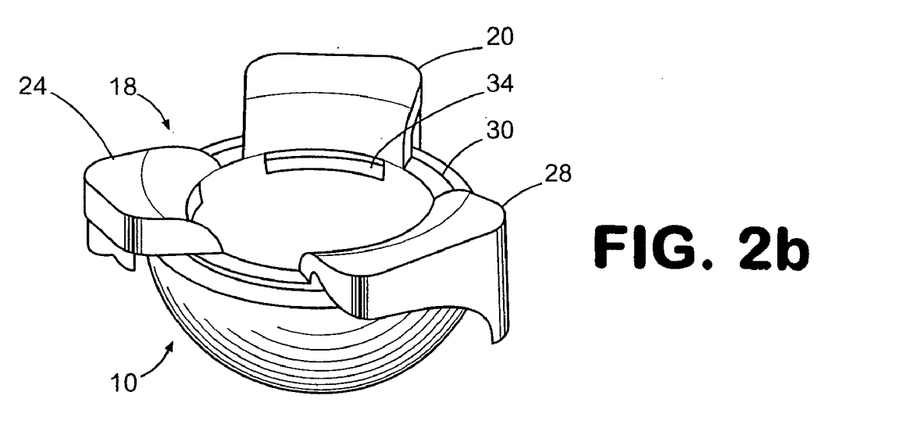
Figure 2C:
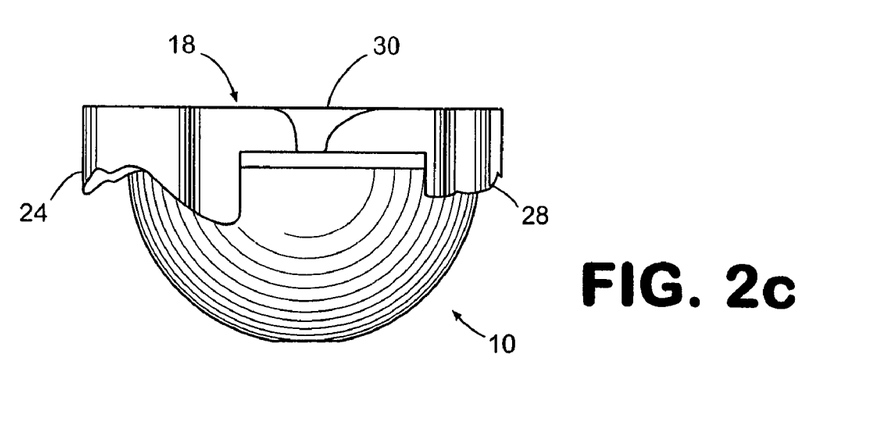
Figure 3A:
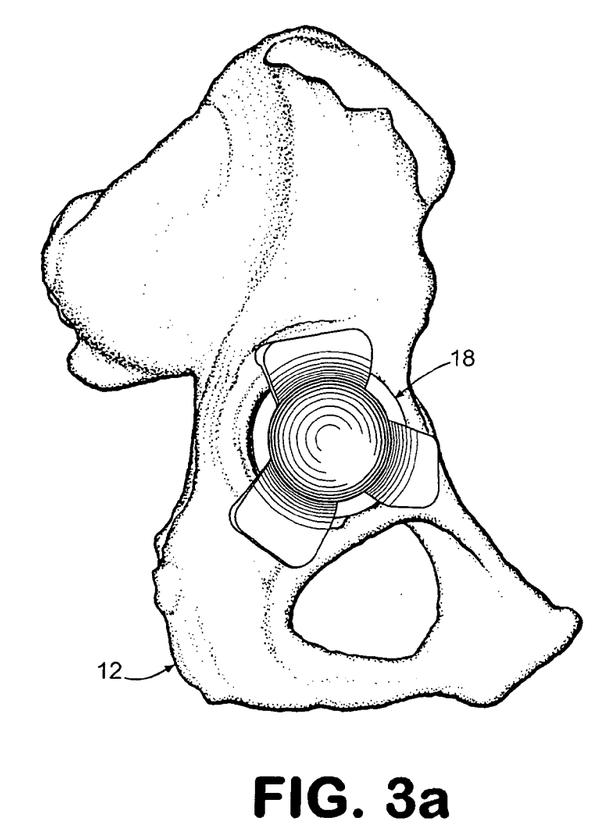
FIGS. 3a, 3b, and 3c are perspective views of a surgical guide image integrated with the bone surface shown in FIGS. 1a, 1b, and 1c, respectively.
Figure 3B:
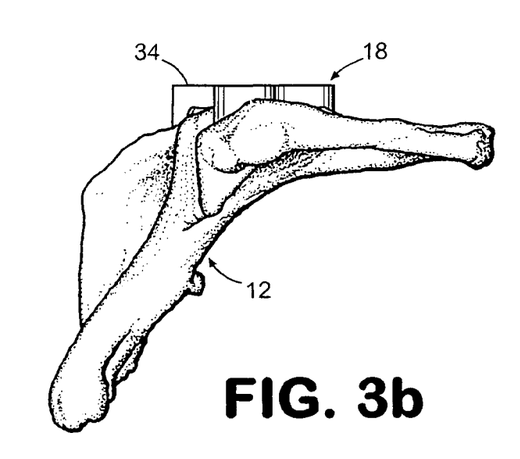
Figure 3C:
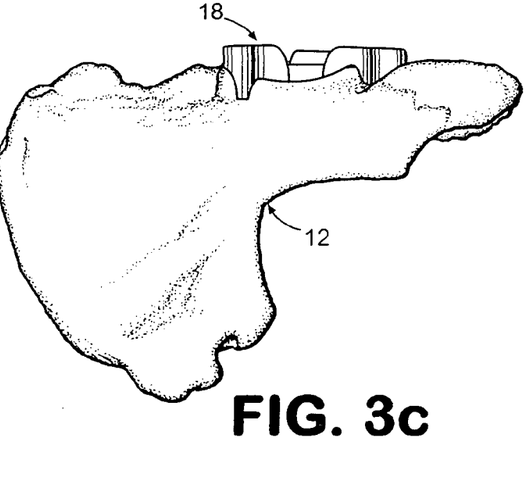

FIG. 2a shows a bottom view of the acetabular cup image 10 as may be seen on the display of a CAD system. The cup image 10 may be rotated to provide the side view shown in FIG. 2c. This view and the perspective shown in FIG. 2b may be used to generate a surgical guide image, such as the acetabular guide image 18 shown in FIGS. 2a, 2b, and 2c, to the cavity within the cup image 10. The guide image 18 includes flanges 20, 24, and 28. The outside diameter of the cup portion 30 of guide image 18 may be generated by reducing the contours of cup image 10 so that it has clearance with respect to the acetabular bone. The inside diameter is reduced from the outside diameter so the thickness t of cup portion 30 is uniform. This thickness may extend laterally from cup portion 30 to form the flanges 20, 24, and 28. The resulting image may be rotated and placed by the CAD software into the acetabulum bone shown in FIGS. 3a, 3b, and 3c. While viewing the composite image, an operator may remove portions of the flanges 20, 24, and 28 so the bottom surface of these flanges complement the undulations in the bone surface image of FIGS. 1a, 1b, and 1c. The resulting fit of the acetabular surgical guide 18 within acetabular cup 10 and on the acetabulum is shown in FIGS. 3a, 3b, and 3c.

The junction between the flanges 20, 24, and 28 and the acetabular cup 30 may also be modified to form marker slots 34 therein. These marker slots 34 are preferably formed so the top lip of the slot is flush with the top rim of the actebular cup of the prosthesis. To form a cavity in the acetabulum to receive the acetabular cup, the surgical guide may be placed on the acetabulum so its undersurface engages and fits the undulations of the acetabulum. Because the design method of the present invention forms the undersurface of the flanges so they complement the undulations in the bone surface with which they mate, the positioning of the surgical guide on the acetabulum is unique. By inscribing the bone through the marker slots and along the rim of the acetabular cup portion 30, a surgeon is able to mark a staggered line on the acetabular bone where the rim of the acetabular cup 10 should rest. The staggered marking aids the surgeon in cup placement because the slot marks are covered and the rim marks are visible when the cup 10 is in the proper position. This alignment enables a surgeon to view the proper angular orientation and depth in the acetabulum for the acetabular cup 10. By referring to this line, the surgeon is able to ream the cavity for the acetabular cup with relative confidence that the cavity is oriented and sized appropriately for receiving the acetabular cup.

Figure 4A:
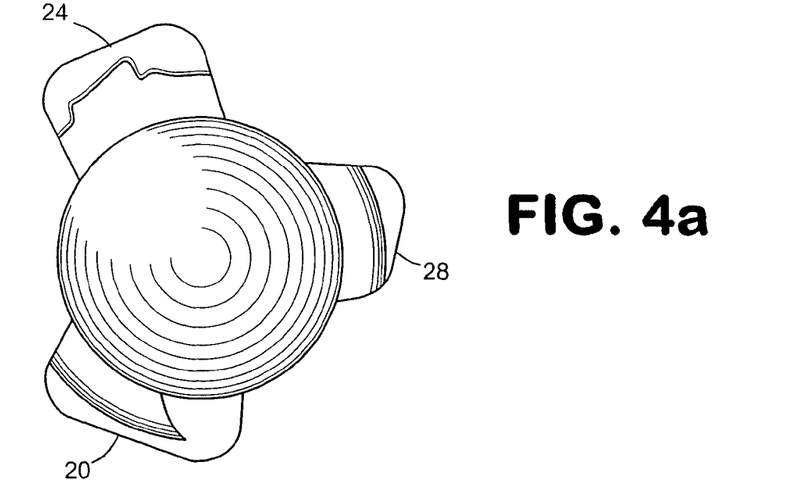
FIGS. 4a, 4b, and 4c are perspective views of the surgical guide image of FIGS. 1a, 1b, and 1c.
Figure 4B:
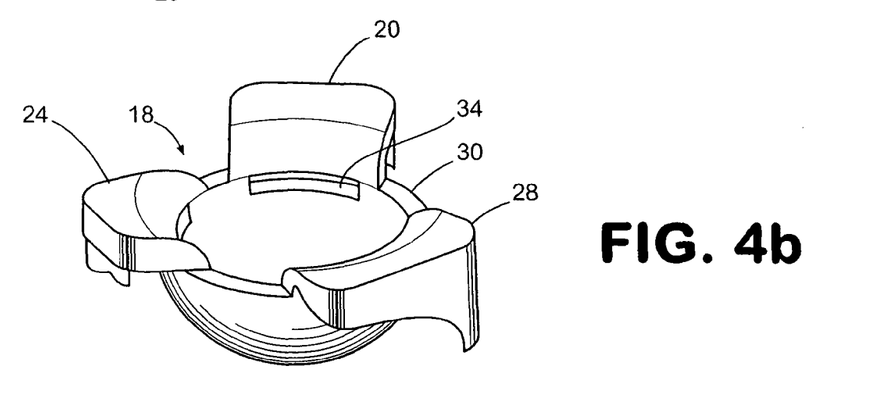
Figure 4C:
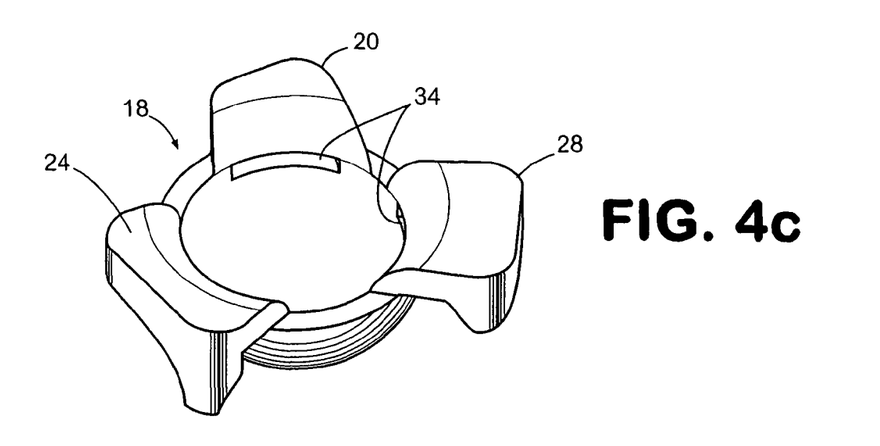

A three dimensional image of a surgical guide may be generated from the bone surface image and an image of a prosthesis to be implanted in the bone corresponding to the bone surface image. The surgical guide image may be viewed without the surrounding bone or prosthesis. As shown in FIGS. 4a, 4b, and 4c, a three dimensional image of a surgical guide may be shown in isolation from the bone surface and prosthesis. FIG. 4a depicts the underside of the flanges 20, 24, and 28 with areas resting on the bone surface being highlighted in a solid color. The areas not resting on the bone surface are shown as white areas. The surgical guide image may be converted and output as control data. One output option of the CAD system for the CAD file describing the three dimensional image of a surgical guide is a stereolithography file format. The Unigraphics CAD system described above has an output option to generate such a file.

The stereolithographic file describing the surgical guide image may be used to operate a stereolithography system. The data from the file control the operation of a laser so the laser selectively crystallizes a resin to form the surgical guide. Alternatively, mechanical cutting tools may be controlled to selectively cut metal or other solid material, such as polyethylene, for example, to form the surgical guide. The material used to form the surgical guide must be capable of being sterilized so the risk of infection from the surgical guide is minimized.

Figure 5:
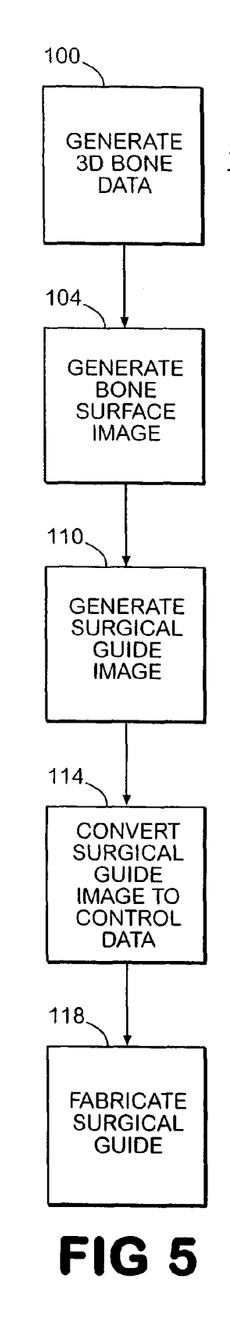
FIG. 5 is a flow chart of an exemplary method for implementing the principles of the present invention.

A method for designing a surgical guide is shown in FIG. 5. The process includes the generation of three dimensional bone anatomical data for a patient's bone (block 100). The patient's bone anatomical data are converted into a bone surface image (block 104). An image of a prosthesis to be implanted in the bone is imposed on the bone surface image and a surgical guide image is generated to conform the supporting structure of the surgical guide image to surface features of the bone surface image (block 110). The resulting surgical guide image may then be converted into control data (block 114). Control data in the form of stereolithography data may be used to control a laser to selectively crystallize a resin to form a surgical guide that corresponds to the surgical guide image. Control data in the form of machine tool control data may be used to cut a solid material, such as polyethylene, to form a surgical guide that corresponds to the surgical guide image (block 118).

Figure 6:
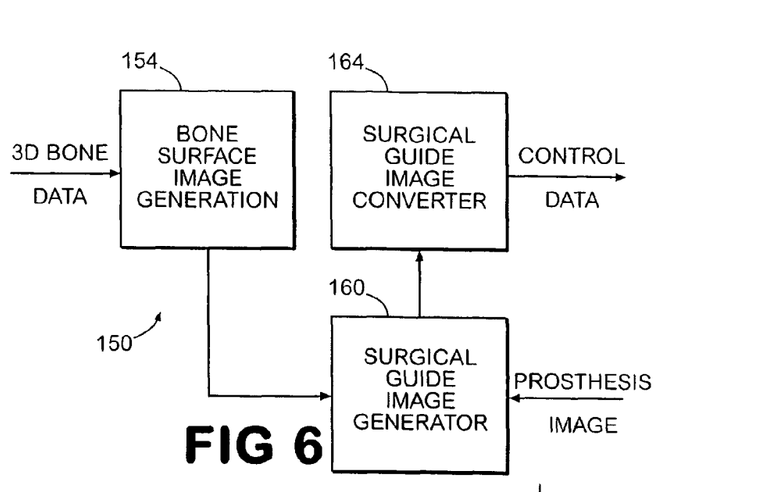
FIG. 6 is a block diagram of a system incorporating the principles of the present invention.

A system for designing and manufacturing a surgical guide is shown in FIG. 6. System 150 includes a bone surface image generator 154, a surgical guide image generator 160, and a surgical guide image converter 164. The bone surface image generator 154 receives bone anatomical data for a patient's bone and generates a bone surface image. Surgical guide image generator 160 generates a surgical guide image from the bone surface image and an image of a prosthesis imposed on the bone surface image. The supporting structure of the generated surgical guide image conforms to the surface features of the three dimensional bone surface image. The surgical guide image is converted by surgical guide image converter 164 into control data for operating a machine to form a surgical guide that corresponds to the surgical guide image.

In a preferred implementation of system 150, the bone image generator 154 is a computer program such as the Mimics program described above. Also in a preferred implementation, the surgical guide image generator 160 and the surgical guide image converter 164 are functions of a CAD system program, such as the Imageware software in the Unigraphics CAD system discussed above. The control data output by system 150 is preferably stereolithography data that may be used to control a laser for selectively crystallizing a resin to form a surgical guide. However, the control data may be in the form of commands for operating a cutting tool or the like, such as a computerized numerical control (CNC) machine, to form the surgical guide from a solid material that may be sterilized for use in an operating room. For example, the surgical guide may be formed of a conventional bio-compatible metal or a suitably strong material such as polethylene.

Figure 7:
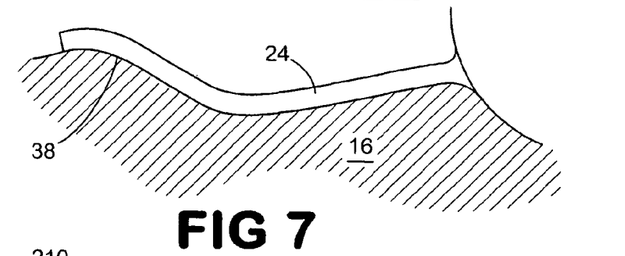
FIG. 7 is a partial, cross-sectional view of the ilium and a flange of the surgical guide image shown in FIGS. 3a, 3b, and 3c.

The bone-facing surfaces of the flanges of a surgical guide made in accordance with the principles of the present invention may each possess a shape that is complementary to a portion of a surface of the corresponding bone. For example, as indicated in FIG. 7, the bone-facing surface 38 of the flange 24 may possess a shape that is complementary to a portion of a surface of the ilium 16. Thus, the shape of the bone-facing surface 38 may follow the contours and undulations of the entire portion of the surface of the ilium 16 that the bone-facing surface 38 contacts.

The bone anatomical data corresponding to a patient's bone may be generated by any device that produces three dimensional data that define at least the relevant part of the patient's bone in which a prosthesis will be implanted, namely the portion of the bone that is engaged by the surgical guide. As is well known in the art, anatomical bone data may be produced by an anatomical bone data generator, such as a CT scanner, that generates a series of two-dimensional data slices from various scanning orientations and three-dimensional scan data may be generated from the oriented stack of two-dimensional data slices.

For a hip replacement procedure, the three-dimensional scan data may define the entire innominate bone, and may include certain thickness information that is not needed in order to design the surgical guide. The three-dimensional scan data may also include data defining other bone structures or other body parts that also are irrelevant to the design of the surgical guide. The bone surface image generator may also include surfacing software that extracts a set of three-dimensional surface data defining at least the relevant part of the surface of the patient's innominate bone from the three-dimensional scan data.

In a preferred embodiment of system 150, the surgical guide image generator may use a standardized design for a prosthetic component to be implanted in the patient's bone, such as an acetabular cup, from which the surgical guide image is, at least partially, formed. That is, the prosthetic component design may have standardized dimensions familiar to the surgeon. The system 150 may share a housing with either an anatomical data generator or the surgical guide fabricating apparatus. Alternatively, the system 150 may be a stand-alone unit that is disposed outside the housing of an anatomical data generator and a surgical guide fabricating apparatus.

Figure 8:
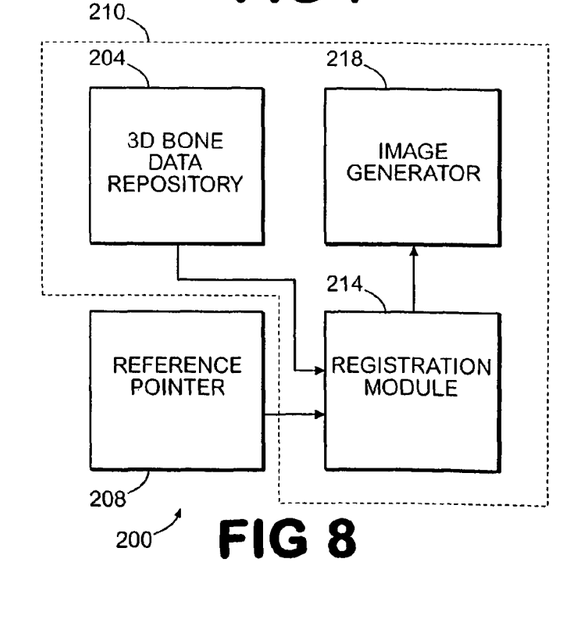
FIG. 8 is a block diagram of a system for visually assisting a surgeon with a joint replacement operation.

A system for assisting a surgeon in the performance of a joint replacement surgery is shown in FIG. 8. The system 200 includes a patient bone data repository 204, a reference pointer 208, and a computer 210 having a registration module 214 and an image generator 218. Patient bone data repository 204 contains bone anatomical image data for a patient's bone, such as CT data of the patient's joint. Preferably, this data is converted and stored in repository 204 in a three dimensional volumetric format, sometimes called voxel data. The registration module 214 and the image generator 218 are preferably computer programs that are executed in the computer 210, although they may be implemented in separate units having their own processors, memory, and programs. An exemplary computer for implementing system 200 is one having a Pentium processor running at 4 GHz with 128 MB of RAM and a 60 GB hard drive, although other computer systems may be used as long as they are able to perform the requisite functions within a reasonable period of time. The reference pointer 208 is coupled to the computer 210 to provide signals regarding the placement of the tip of the reference pointer 208. The reference pointer 208 may be implemented with an articulating arm having positional gyros at each arm joint to provide positional data regarding movement of an articulating arm joint. These positional data are used to determine the movement of the tip of the reference pointer 208 in space. The reference pointer 208 may also be implemented with a wireless device that transmits positional data regarding the pointer's location. Positional data from the reference pointer 208 may be received and processed by the computer 210 to correlate pointer position to the image data stored in the repository 204.

The registration module 214 receives positional data from the reference pointer 208 and correlates a position corresponding to the positional data to a point on the surface of the volumetric image stored in the repository 204. At least three surface points are required for the registration module 214 to establish a correlation between the volumetric image stored in the repository 204 and the surgical site. The registration module 204 performs this function by receiving positional data from the reference pointer 208 and correlating the positional data to the image data stored in the repository 204 so the three dimensional patient bone data may be oriented to the patient's body position on the surgical table. Once registration is achieved, an image may be generated from any perspective. The perspective may be defined by an angular orientation of the reference pointer 208 or it may be specified by the surgeon.

The image generator 218 receives the volumetric image data and requested image orientation and generates an image that is presented on a display associated with the computer 210. The image generator 218 may also be selectively activated to impose image data for the prosthetic being implanted. This image enables the surgeon to compare an image of what the surgical site looks like with the prosthetic implanted to the actual surgical site. The surgeon then is able to form a better idea of what must be removed to adapt the bone for the implant. As bone is removed, the registration module 214 determines that the surface points of the volumetric data are changing. Consequently, the image presented by the image generator 218 changes to show the surgeon the changes to the implant site and what remains to be removed before the site is ready to receive the implant.

Figure 9A:
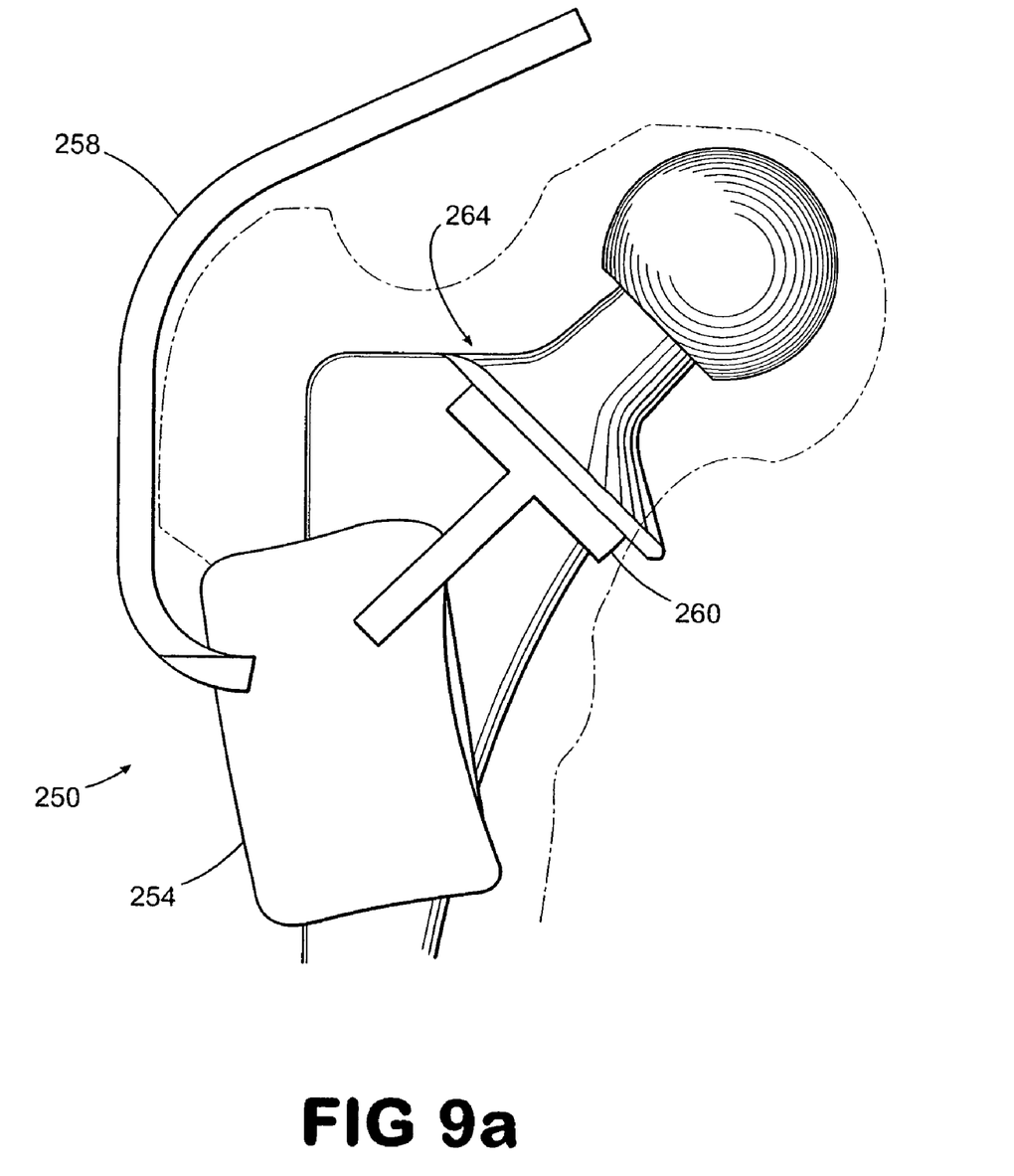
FIGS. 9a, 9b, and 9c are perspective views of a surgical guide image integrated with a femoral bone surface image.
Figure 9B:
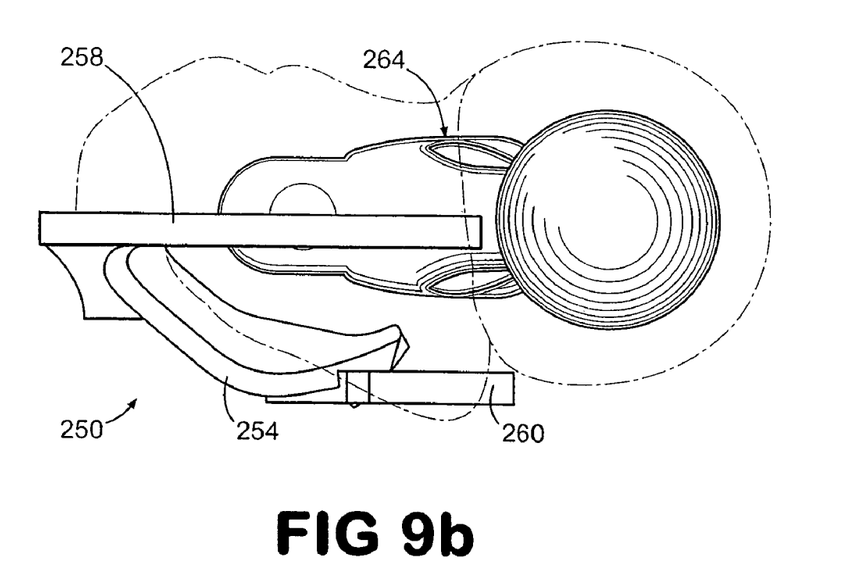
Figure 9C:
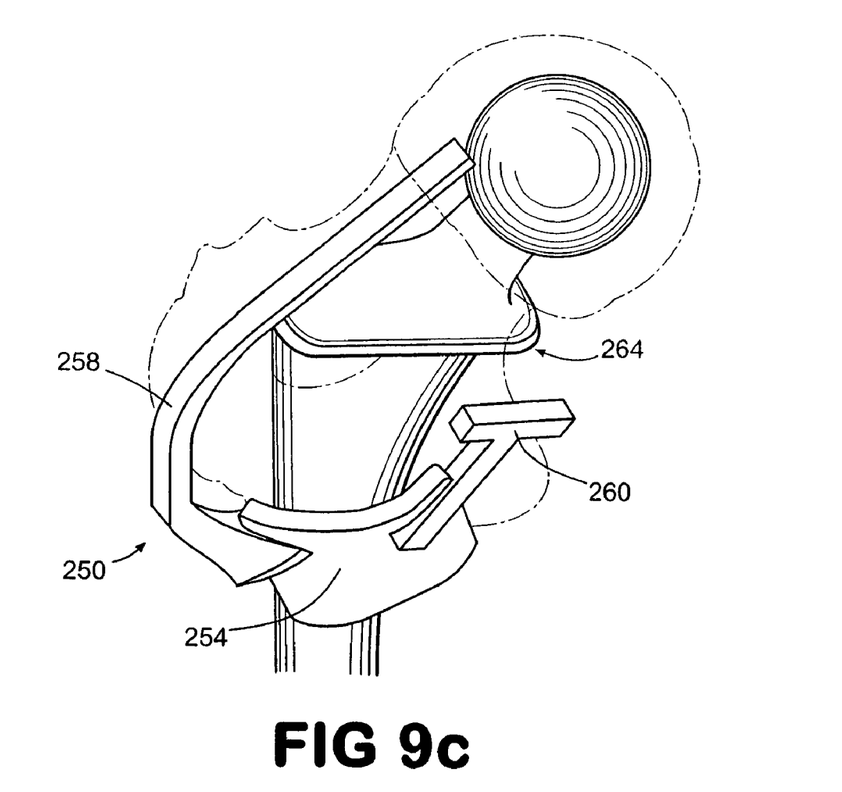

While an implementation of the present invention has been described with particular reference to a surgical guide for implantation of an acetabular cup, the system and method may be used to design and fabricate other surgical guides for other prosthetic implants. For example, a surgical implant for aligning a femoral stem implant to replace the head of a femur is shown in FIG. 9. As shown in FIG. 9a, femur stem guide image 250 may include a jig pad 254, an alignment arm 258, and a resection marker 260. Again, bone anatomical data for a patient's femur is used to generate a bone surface image so bony landmarks may be identified for the surgical guide. A prosthetic implant image, such as femoral stem image 264, may be imposed on the bone surface image so a surgical guide image for a femoral stem may be generated. In the case of a femoral stem implant, the jig pad 254 is generated so its surface complements the patient's femur and uniquely positions the surgical guide on the femur remaining after the femoral head is cut off for stem implantation. The alignment arm 258 provides a visual reference for the angular orientation of the femoral stem when it is properly positioned in the femur. The resection marker 260 identifies a line for removing the head of the patient's femur. FIGS. 9b and 9c provide additional perspective views for understanding how guide 250 is placed on a femur to assist a surgeon in the implantation of a femoral stem. Jig pad 254 is placed sufficiently close to the femoral head that bony landmarks are available for ensuring unique placement of the surgical guide but not so close that the landmarks are removed during resection of the femoral head. Preferably, the lesser trochanter defines the outer boundary for bony landmarks for a femoral stem.

While the invention has been illustrated and described in detail in the drawings and foregoing description, the same should be considered as illustrative and not restrictive in character. The reader should understand that only the preferred embodiments have been presented and that all changes, modifications and further applications that come within the spirit of the invention are desired to be protected. For instance, while the present invention is shown and described with respect to a hip joint, it should be understood that the principles of the subject invention as described herein are applicable to prostheses for joints other than the hip.

What is claimed is:

1. A method for designing a surgical guide for a joint replacement prosthesis comprising:
    generating a bone surface image from three dimensional bone image data of a patient's bone;
    generating a surgical guide image from the bone surface image and an image of a prosthetic implant imposed on the bone surface image; and
    generating control data from the generated surgical guide image, the control data being used to control operation of a machine to fabricate a surgical guide.

2. The method of claim 1, wherein the bone surface image is formed from computed tomography data of the patient's bone.

3. The method of claim 1, wherein the surgical guide image generation includes integrating at least one marker slot in the surgical guide image.

4. The method of claim 1 further comprising:
    controlling a laser with the control data to selectively crystallize a resin to form a surgical guide that corresponds to the surgical guide image.

5. The method of claim 1 further comprising:
    controlling a machine tool with the control data to selectively cut a solid material to form a surgical guide that corresponds to the surgical guide image.

6. The method of claim 1 wherein the control data generation includes:
    generating stereolithography data from the surgical guide image.

7. The method of claim 1 wherein the control data generation includes:
    generating machine tool control data from the surgical guide image.

8. A system for designing a surgical guide for a joint replacement prosthesis comprising:
    a bone surface image generator for forming a bone surface image from three dimensional bone anatomical data for a patient's bone;
    a surgical guide image generator for generating a surgical guide image from the bone surface image and an image of a prosthesis implant imposed on the bone surface image; and
    a surgical guide image converter for generating control data to control operation of a machine for fabricating a surgical guide that corresponds to the surgical guide image.

9. The system of claim 8, wherein the bone surface image generator generates a bone surface image from computed tomography data of a patient's bone.

10. The system of claim 8, wherein the surgical guide image generator integrates at least one marker slot in the surgical guide image.

11. The system of claim 8 wherein the control data generator generates stereolithography data for controlling a laser to selectively crystallize a resin to form the surgical guide.

12. The system of claim 8 wherein the control data generator generates computerized numerical control data for controlling a cutting tool to selectively cut a solid material to form the surgical guide.

13. The system of claim 8 wherein the surgical guide image generator generates the surgical guide image from a bone surface image of an acetabulum bone and an image of an acetabular cup.

14. The system of claim 8 wherein the surgical guide image generator generates the surgical guide image from a bone surface image of a femur bone and an image of a femoral stem.

15. A system for aiding a surgeon in a joint replacement operation comprising:
    a patient bone data repository for storing three dimensional data of a patient's bone;
    a reference pointer for providing positional data of a surgical site;
    a registration module for (i) receiving the positional data, (ii) correlating the positional data for the surgical site obtained from the reference pointer to the three dimensional data for the bone stored in the patient bone repository, and (iii) determining changes in the surface of the bone; and
    an image generator for generating an image of the patient's bone with an image of a prosthetic implant imposed on the image of the patient's bone.

16. The system of claim 15 wherein the image generator generates the image in an orientation that corresponds to the angular orientation of the reference pointer with respect to a position on the bone.

17. The system of claim 15 wherein the reference pointer is an articulating arm with positional gyros mounted at pivotal joints of the articulating arm.

18. The system of claim 15 wherein the reference pointer communicates wirelessly with the registration module.

19. The system of claim 15 wherein the image generator generates an image of an acetabular cup on an image of a patient's acetabulum bone.

20. The system of claim 15, wherein the registration module is further configured to identify the portion of a bone remaining to be excised based upon the received positional data.

* * * * *